US012678450B2

(12) United States Patent
Checketts et al.

(10) Patent No.: US 12,678,450 B2
(45) Date of Patent: Jul. 14, 2026

(54) USE OF CANNABIDIOL IN THE TREATMENT OF SEIZURES ASSOCIATED WITH RARE EPILEPSY SYNDROMES RELATED TO GENETIC ABNORMALITIES

(71) Applicant: Jazz Pharmaceuticals Research UK Limited, Sittingbourne (GB)

(72) Inventors: Daniel Adam Checketts, Sittingbourne (GB); Kevin James Craig, Sittingbourne (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 605 days.

(21) Appl. No.: 18/005,853

(22) PCT Filed: Jul. 15, 2021

(86) PCT No.: PCT/EP2021/069889
§ 371 (c)(1),
(2) Date: Jan. 18, 2023

(87) PCT Pub. No.: WO2022/017952
PCT Pub. Date: Jan. 27, 2022

(65) Prior Publication Data
US 2023/0285425 A1 Sep. 14, 2023

(30) Foreign Application Priority Data
Jul. 20, 2020 (GB) ..................................... 2011161

(51) Int. Cl.
| | |
|---|---|
| A61K 31/00 | (2006.01) |
| A61K 31/197 | (2006.01) |
| A61K 31/55 | (2006.01) |
| A61K 45/06 | (2006.01) |
| A61P 25/08 | (2006.01) |

(52) U.S. Cl.
CPC .......... *A61K 31/658* (2023.05); *A61K 31/197* (2013.01); *A61K 31/55* (2013.01); *A61K 45/06* (2013.01); *A61P 25/08* (2018.01)

(58) Field of Classification Search
CPC .... A61K 31/658; A61K 31/197; A61K 31/55; A61K 45/06; A61K 25/08; A61K 31/05; A61K 36/185; A61K 25/10; A61K 25/12; A61K 2300/00
See application file for complete search history.

(56) References Cited

U.S. PATENT DOCUMENTS

| | | | |
|---|---|---|---|
| 8,632,825 | B2 | 1/2014 | Velasco Diez et al. |
| 8,790,719 | B2 | 7/2014 | Parolaro et al. |
| 9,017,737 | B2 | 4/2015 | Kikuchi et al. |
| 9,125,859 | B2 | 9/2015 | Whalley et al. |
| 9,474,726 | B2 | 10/2016 | Guy et al. |
| 9,675,654 | B2 | 6/2017 | Parolaro et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado et al. |
| 10,226,433 | B2 | 3/2019 | Di Marzo et al. |
| 10,583,096 | B2 | 3/2020 | Guy et al. |
| 10,603,288 | B2 | 3/2020 | Guy et al. |
| 10,653,641 | B2 | 5/2020 | Robson et al. |
| 10,709,671 | B2 | 7/2020 | Guy et al. |
| 10,709,673 | B2 | 7/2020 | Guy |
| 10,709,674 | B2 | 7/2020 | Guy et al. |
| 10,729,665 | B2 | 8/2020 | Whalley et al. |
| 10,758,514 | B2 | 9/2020 | Liu et al. |
| 10,765,643 | B2 | 9/2020 | Guy et al. |
| 10,799,467 | B2 | 10/2020 | Whalley et al. |
| 10,807,777 | B2 | 10/2020 | Whittle |

(Continued)

FOREIGN PATENT DOCUMENTS

| | | |
|---|---|---|
| GB | 2531278 A | 4/2016 |
| GB | 2531282 A | 4/2016 |

(Continued)

OTHER PUBLICATIONS

Baldassari, S. et al., "The landscape of epilepsy-related GATOR1 variants," Genet Med., 21(2):398-408 (2019); doi:10.1038/s41436-018-0060-2. Epub Aug. 10, 2018.

Bonaglia, M. C. et al., "Partial deletion of DEPDC5 in a child with focal epilepsy," Epilepsia Open, 1(3-4):140-144 (2016). Published online Aug. 25, 2016. doi: 10.1002/epi4.12012.

Caraballo, R. et al., "Effectiveness of cannabidiol in a prospective cohort of children with drug resistant epileptic encephalopathy in Argentina," Seizure: European Journal of Epilepsy, 80:75-80 (2020).

Eadie, M. J., "Shortcomings in the current treatment of epilepsy," Expert Rev Neurother., 12(12):1419-1427 (2012).

Elsohly, M. & Gul, W., Handbook of Cannabis, Chapter 1, Constituents of Cannabis Sativa, Roger Pertwee, Ed., 2012, 21 pages.

EPIDIOLEX® (cannabidiol) oral solution, CV, Prescribing Information, 2018, 30 pages; https://www.accessdata.fda.gov/drugsatfda_docs/label/2018/210365lbl.pdf.

(Continued)

*Primary Examiner* — Aradhana Sasan
(74) *Attorney, Agent, or Firm* — COOLEY LLP

(57) ABSTRACT

The present invention relates to the use of cannabidiol (CBD) for the treatment of seizures associated with rare epilepsy syndromes. In particular the seizures associated with rare epilepsy syndromes that are treated are those which are experienced inpatients diagnosed with autosomal dominant nocturnal frontal lobe epilepsy (ADNFLE) with DEPDC5 gene mutation. In a further embodiment the types of seizures include tonic, tonic-clonic and focal seizures without impairment. Preferably the dose of CBD is between 5 mg/kg/day to 50 mg/kg/day.

15 Claims, No Drawings

(56) References Cited

U.S. PATENT DOCUMENTS

| | | | |
|---|---|---|---|
| 10,849,860 B2 | 12/2020 | Guy et al. | |
| 10,918,608 B2 | 2/2021 | Guy et al. | |
| 10,966,939 B2 | 4/2021 | Guy et al. | |
| 11,000,486 B2 | 5/2021 | Wright et al. | |
| 11,065,209 B2 | 7/2021 | Guy et al. | |
| 11,065,227 B2 | 7/2021 | Stott et al. | |
| 11,096,905 B2 | 8/2021 | Guy et al. | |
| 11,147,776 B2 | 10/2021 | Stott et al. | |
| 11,147,783 B2 | 10/2021 | Stott et al. | |
| 11,154,516 B2 | 10/2021 | Guy et al. | |
| 11,154,517 B2 | 10/2021 | Guy et al. | |
| 11,160,757 B1 | 11/2021 | Wilkhu et al. | |
| 11,160,795 B2 | 11/2021 | Guy et al. | |
| 11,207,292 B2 | 12/2021 | Guy et al. | |
| 11,229,612 B2 | 1/2022 | Wright et al. | |
| 11,291,631 B2 | 4/2022 | Shah | |
| 11,311,498 B2 | 4/2022 | Guy et al. | |
| 11,318,109 B2 | 5/2022 | Whalley et al. | |
| 11,357,741 B2 | 6/2022 | Guy et al. | |
| 11,400,055 B2 | 8/2022 | Guy et al. | |
| 11,406,623 B2 | 8/2022 | Guy et al. | |
| 11,413,266 B2 | 8/2022 | Biró et al. | |
| 11,419,829 B2 | 8/2022 | Whalley et al. | |
| 11,426,362 B2 | 8/2022 | Wright et al. | |
| 11,446,258 B2 | 9/2022 | Guy et al. | |
| 11,590,087 B2 | 2/2023 | Guy et al. | |
| 11,633,369 B2 | 4/2023 | Guy et al. | |
| 11,679,087 B2 | 6/2023 | Guy et al. | |
| 11,684,598 B2 | 6/2023 | Stott et al. | |
| 11,701,330 B2 | 7/2023 | Guy et al. | |
| 11,766,411 B2 | 9/2023 | Guy et al. | |
| 11,793,770 B2 | 10/2023 | Stott et al. | |
| 11,806,319 B2 | 11/2023 | Wilkhu et al. | |
| 11,865,102 B2 | 1/2024 | Guy et al. | |
| 2015/0359756 A1 | 12/2015 | Guy et al. | |
| 2017/0231923 A1* | 8/2017 | Guy | A61P 25/10 514/94 |
| 2017/0239193 A1 | 8/2017 | Guy et al. | |
| 2018/0071210 A1 | 3/2018 | Wilkhu et al. | |
| 2018/0228751 A1 | 8/2018 | Stott et al. | |
| 2019/0167583 A1 | 6/2019 | Shah | |
| 2019/0314296 A1 | 10/2019 | Wright et al. | |
| 2019/0321307 A1 | 10/2019 | Guy et al. | |
| 2019/0365667 A1 | 12/2019 | Wright et al. | |
| 2020/0138738 A1 | 5/2020 | Guy et al. | |
| 2020/0179303 A1 | 6/2020 | Guy et al. | |
| 2020/0206153 A1 | 7/2020 | Whalley et al. | |
| 2020/0237683 A1 | 7/2020 | Whalley et al. | |
| 2020/0297656 A1 | 9/2020 | Guy et al. | |
| 2020/0352878 A1 | 11/2020 | Guy et al. | |
| 2021/0015789 A1 | 1/2021 | Guy et al. | |
| 2021/0052512 A1 | 2/2021 | Guy et al. | |
| 2021/0059949 A1 | 3/2021 | Wilkhu et al. | |
| 2021/0059960 A1 | 3/2021 | Wilkhu et al. | |
| 2021/0059976 A1 | 3/2021 | Wilkhu et al. | |
| 2021/0069333 A1 | 3/2021 | Velasco Diez et al. | |
| 2021/0100755 A1 | 4/2021 | Whalley et al. | |
| 2021/0169824 A1 | 6/2021 | Guy et al. | |
| 2021/0177773 A1 | 6/2021 | Guy et al. | |
| 2021/0290565 A1 | 9/2021 | Guy et al. | |
| 2021/0308072 A1 | 10/2021 | Wright et al. | |
| 2021/0330636 A1 | 10/2021 | Guy et al. | |
| 2021/0401771 A1 | 12/2021 | Guy et al. | |
| 2022/0000800 A1 | 1/2022 | Guy et al. | |
| 2022/0008355 A1 | 1/2022 | Guy et al. | |
| 2022/0016048 A1 | 1/2022 | Guy et al. | |
| 2022/0023232 A1 | 1/2022 | Guy et al. | |
| 2022/0040155 A1 | 2/2022 | Guy et al. | |
| 2022/0062197 A1 | 3/2022 | Stott et al. | |
| 2022/0062211 A1 | 3/2022 | Stott et al. | |
| 2022/0087951 A1 | 3/2022 | Knappertz | |
| 2022/0096397 A1 | 3/2022 | Wright et al. | |
| 2022/0168266 A1 | 6/2022 | Guy et al. | |
| 2022/0183997 A1 | 6/2022 | Guy et al. | |
| 2022/0184000 A1 | 6/2022 | Guy et al. | |
| 2022/0202738 A1 | 6/2022 | Guy et al. | |
| 2022/0211629 A1 | 7/2022 | Wilkhu et al. | |
| 2022/0226257 A1 | 7/2022 | Guy et al. | |
| 2022/0233495 A1 | 7/2022 | Silcock et al. | |
| 2022/0249396 A1 | 8/2022 | Guy et al. | |
| 2022/0257529 A1 | 8/2022 | Guy et al. | |
| 2022/0265573 A1 | 8/2022 | Guy et al. | |
| 2022/0288055 A1 | 9/2022 | Silcock et al. | |
| 2022/0378714 A1 | 12/2022 | Guy et al. | |
| 2022/0378715 A1 | 12/2022 | Guy et al. | |
| 2022/0378738 A1 | 12/2022 | Guy et al. | |
| 2022/0387347 A1 | 12/2022 | Whalley et al. | |
| 2022/0395470 A1 | 12/2022 | Whalley et al. | |
| 2022/0395471 A1 | 12/2022 | Guy et al. | |
| 2023/0000789 A1 | 1/2023 | Guy et al. | |
| 2023/0022487 A1 | 1/2023 | Guy et al. | |
| 2023/0024312 A1 | 1/2023 | Whalley et al. | |
| 2023/0026079 A1 | 1/2023 | Guy et al. | |
| 2023/0032502 A1 | 2/2023 | Guy et al. | |
| 2023/0038423 A1 | 2/2023 | Silcock et al. | |
| 2023/0068885 A1 | 3/2023 | Guy et al. | |
| 2023/0143812 A1 | 5/2023 | Knappertz et al. | |
| 2023/0235825 A1 | 7/2023 | Thompson et al. | |
| 2023/0248664 A1 | 8/2023 | Guy | |
| 2023/0263744 A1 | 8/2023 | Guy | |
| 2023/0277560 A1 | 9/2023 | Checketts et al. | |
| 2023/0277561 A1 | 9/2023 | Checketts et al. | |
| 2023/0277562 A1 | 9/2023 | Checketts et al. | |
| 2023/0277563 A1 | 9/2023 | Checketts et al. | |
| 2023/0285419 A1 | 9/2023 | Checketts et al. | |
| 2023/0285420 A1 | 9/2023 | Checketts et al. | |
| 2023/0285421 A1 | 9/2023 | Checketts et al. | |
| 2023/0285422 A1 | 9/2023 | Checketts et al. | |
| 2023/0285423 A1 | 9/2023 | Checketts et al. | |
| 2023/0285424 A1 | 9/2023 | Checketts et al. | |
| 2023/0285426 A1 | 9/2023 | Checketts et al. | |
| 2023/0285427 A1 | 9/2023 | Checketts et al. | |
| 2023/0285428 A1 | 9/2023 | Checketts et al. | |
| 2023/0301934 A1 | 9/2023 | Whalley et al. | |
| 2023/0301936 A1 | 9/2023 | Guy | |
| 2023/0310464 A1 | 10/2023 | Checketts et al. | |
| 2023/0372367 A1 | 11/2023 | Checketts et al. | |
| 2023/0372368 A1 | 11/2023 | Checketts et al. | |
| 2024/0016819 A1 | 1/2024 | Craig | |
| 2024/0025858 A1 | 1/2024 | Silcock et al. | |
| 2024/0033229 A1 | 2/2024 | Guy et al. | |
| 2024/0033272 A1 | 2/2024 | Checketts et al. | |
| 2024/0043388 A1 | 2/2024 | Silcock et al. | |
| 2024/0050452 A1 | 2/2024 | Craig et al. | |

FOREIGN PATENT DOCUMENTS

| | | | | |
|---|---|---|---|---|
| WO | WO-2016176279 A1 * | 11/2016 | | A61K 9/0095 |
| WO | WO-2019207319 A1 | 10/2019 | | |
| WO | WO-2020109806 A1 | 6/2020 | | |

OTHER PUBLICATIONS

Hausman-Kedem, M. et al., "Efficacy of CBD-enriched medical cannabis for treatment of refractory epilepsy in children and adolescents—An observational, longitudinal study," Brain Dev., 40(7):544-551 (2018); doi: 10.1016/j.braindev.2018.03.013. Epub Apr. 16, 2018.

Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.

Laux, L. C. et al., "Long-term safety and efficacy of cannabidiol in children and adults with treatment resistant Lennox-Gastaut syndrome or Dravet syndrome: Expanded access program results," Epilepsy Research, 154:13-20 (2019).

Pertwee, R. G., "The Pharmacology and Therapeutic Potential of Cannabidiol," Cannabinoids, Chapter 3, DiMarzo, V. (Ed.), pp. 32-83 (2004).

(56) References Cited

OTHER PUBLICATIONS

Picard, F. et al., "DEPDC5 mutations in families presenting as autosomal dominant nocturnal frontal lobe epilepsy," Neurology, 82:2101-2106 (2014).

Porter, B. E. & Jacobson, C., "Report of a parent survey of cannabidiol-enriched cannabis use in pediatric treatment-resistant epilepsy," Epilepsy Behav., 29(3):574-577 (2013).

Rosenberg, E. C. et al., "Quality of Life of Childhood Epilepsy (QOLCE) in pediatric patients enrolled in a prospective, open-label clinical study with cannabidiol (CBD)," Epilepsia, 58(8):e96-e100 (2017); doi:10.1111/epi.13815.

Silvestro, S. et al., "Use of Cannabidiol in the Treatment of Epilepsy: Efficacy and Security in Clinical Trials," Molecules, 24:1459 (2019), 25 pages; doi:10.3390/molecules24081459.

Stockings, E. et al., "Evidence for cannabis and cannabinoids for epilepsy: a systematic review of a controlled and observational evidence," J. Neurol Neurosurg Psychiatry, 89:741-753 (2018); doi: 10.1136/jnnp-2017-317168.

Szaflarski, J. P. et al., "Long-term safety and treatment effects of cannabidiol in children and adults with treatment-resistant epilepsies: Expanded access program results," Epilepsia, 59:1540-1548 (2018).

Thurman, D. J. et al., "Standards for epidemiologic studies and surveillance of epilepsy," Epilepsia, 52 (Suppl 7):2-26 (2011).

Chiron, C. & Dulac, O., "The pharmacologic treatment of Dravet syndrome," Epilepsia, 52(Suppl 2):72-5 (Apr. 2011).

Kelley, S. A. & Kossoff, E. H., "Doose syndrome (myoclonic-astatic epilepsy): 40 years of progress," Developmental Med. & Child Neurol., 52(11):988-93 (Nov. 2010).

Lutz, B. et al., "On-demand activation of the endocannabinoid system in the control of neuronal excitability and epileptiform seizures," Biochemical Pharmacology 68:1691-1698 (Nov. 2004).

Mayo Clinic, "Carbamazepine (oral route)," [drug information], provided by Merative, Micromedex®, DRG-20062739, (initial publication date unknown; last updated Feb. 1, 2026). [Retrieved from the Internet on Feb. 12, 2026; at URL: https://www.mayoclinic.org/drugs-supplements/carbamazepine-oral-route/description/drg-20062739], 28 pages.

Mayo Clinic, "Phenytoin (oral route)," [drug information], provided by Merative, Micromedex®, DRG-20072875, (initial publication date unknown; last updated Feb. 1, 2026). [Retrieved from the Internet on Feb. 12, 2026; at URL: https://www.mayoclinic.org/drugs-supplements/phenytoin-oral-route/description/drg-20072875], 24 pages.

Scheffer, I. E. et al., "Autosomal dominant nocturnal frontal lobe epilepsy. A distinctive clinical disorder," Brain, 118(Pt 1):61-73 (Feb. 1995). doi: 10.1093/brain/118.1.61.

U.S. Food and Drug Administration, "What We Do," [website] FDA.gov., U.S. Department of Health and Human Services, (initial publication date unknown; last updated Nov. 21, 2023). [Retrieved from the Internet on Feb. 12, 2026, at URL: https://www.fda.gov/about-fda/what-we-do], 5 pages.

Vossler, D. G. & Gidal, B. E., "A summary of antiseizure medications available in the United States: 4th Edition," American Epilepsy Society, (Revised Apr. 1, 2024), 28 pages.

* cited by examiner

USE OF CANNABIDIOL IN THE TREATMENT OF SEIZURES ASSOCIATED WITH RARE EPILEPSY SYNDROMES RELATED TO GENETIC ABNORMALITIES

CROSS-REFERENCE TO RELATED APPLICATIONS

This application is a U.S. National Phase application, filed under 35 U.S.C. § 371(c), of International Application No. PCT/EP2021/069889, filed Jul. 15, 2021, which claims priority to, and the benefit of, United Kingdom Patent Application No. 2011161.3, filed Jul. 20, 2020. Each of these documents is incorporated by reference herein in its entirety for all purposes.

FIELD OF THE INVENTION

The present invention relates to the use of cannabidiol (CBD) for the treatment of seizures associated with rare epilepsy syndromes. In particular the seizures associated with rare epilepsy syndromes that are treated are those which are experienced in patients diagnosed with autosomal dominant nocturnal frontal lobe epilepsy (ADNFLE) with DEPDC5 gene mutation. In a further embodiment the types of seizures include tonic, tonic-clonic and focal seizures without impairment. Preferably the dose of CBD is between 5 mg/kg/day to 50 mg/kg/day.

In a further embodiment the CBD used is in the form of a highly purified extract of cannabis such that the CBD is present at greater than 95% of the total extract (w/w) and the cannabinoid tetrahydrocannabinol (THC) has been substantially removed, to a level of not more than 0.15% (w/w).

Preferably the CBD used is in the form of a botanically derived purified CBD which comprises greater than or equal to 98% (w/w) CBD and less than or equal to 2% (w/w) of other cannabinoids. More preferably the other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w). The botanically derived purified CBD preferably also comprises a mixture of both trans-THC and cis-THC. Alternatively, a synthetically produced CBD is used.

Most preferably the other cannabinoids present are THC at a concentration of about 0.01% to about 0.1% (w/w); CBD-C1 at a concentration of about 0.1% to about 0.15% (w/w); CBDV at a concentration of about 0.2% to about 0.8% (w/w); and CBD-C4 at a concentration of about 0.3% to about 0.4% (w/w). Most preferably still the THC is present at a concentration of about 0.02% to about 0.05% (w/w).

Where the CBD is given concomitantly with one or more other anti-epileptic drugs (AED), the CBD may be formulated for administration separately, sequentially or simultaneously with one or more AED or the combination may be provided in a single dosage form.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification.

Generalized seizures, where the seizure arises within and rapidly engages bilaterally distributed networks, can be split into six subtypes: tonic-clonic (grand mal) seizures; absence (petit mal) seizures; clonic seizures; tonic seizures; atonic seizures and myoclonic seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace secondary generalized seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Autosomal dominant nocturnal frontal lobe epilepsy (ADNFLE) is an uncommon, inherited form of epilepsy characterized by seizures occurring at night during sleep. Some people with ADNFLE also have seizures during the day. These seizures can last from a few seconds to a few minutes, and can vary from causing simple arousal from sleep, to dramatic muscle spasms and movements.

Most people with ADNFLE have normal intellect, but some affected people have reduced intellect. Some people with ADNFLE also have psychiatric disorders or behavior problems, but it is unclear if these are directly related to ADNFLE.

ADNFLE is inherited in an autosomal dominant manner and may be caused by a mutation in any of several genes. In most cases however, the genetic cause is not found.

The onset of ADNFLE ranges from infancy to adulthood, but most cases begin in childhood and episodes tend to become milder and less frequent with age.

Treatment of ADNFLE involves anti-seizure medications to control seizures. Carbamazepine is usually used as the main drug but oxcarbamazepine, topiramate and acetazolamide may also be used as add-on therapies.

The DEPDC5 gene encodes a protein that is part of a complex, GATOR1, which regulates the mTOR signaling pathway. The mTOR pathway itself is involved in cell growth and proliferation, cell survival, and protein synthesis, including the growth and development of nerve cells and their plasticity. GATOR1 blocks this pathway by inhibiting mTOR complex 1 (mTORC1).

DEPDC5-related epilepsy encompasses a range of epilepsy syndromes, almost all of which are characterized by focal seizures, with seizure onset in a discrete area of the brain. Seizure syndromes include familial focal epilepsy with variable foci (FFEVF), autosomal dominant nocturnal frontal lobe epilepsy (ADNFLE), familial mesial temporal lobe epilepsies (FMTLE), autosomal dominant epilepsy with auditory features (ADEAF), and infantile spasms. Although psychomotor development is usually normal, intellectual disability or autism spectrum disorder has been reported in some individuals.

DEPDC5-related epilepsy is typically inherited in an autosomal dominant manner but de novo DEPDC5 pathogenic variants have also been reported.

The response to antiepileptic drugs (AEDs) is variable in DEPDC5-related epilepsy. While some individuals respond well to first-line AEDs, others are more refractory to treatment. There is currently no evidence that seizures respond better to one particular AED.

Cannabidiol (CBD), a non-psychoactive derivative from the cannabis plant, has demonstrated anti-convulsant properties in several anecdotal reports, pre-clinical and clinical studies both in animal models and humans. Three randomized control trials showed efficacy of the purified pharmaceutical formulation of CBD in patients with Dravet and Lennox-Gastaut syndrome.

Based on these three trials, a botanically derived purified CBD preparation was approved by FDA in June 2018 for the treatment of seizures associated with Dravet and Lennox-Gastaut syndromes.

Documents including WO2020/109806, GB2531282 and GB2531278 disclose the effectiveness of highly purified CBD in the treatment of seizures associated with epileptic syndromes such as Lennox-Gastaut Syndrome. However, there is no data of patients with DEPDC5-related epilepsy nor is there any mention of this condition.

The applicant has found by way of an open label, expanded-access program that treatment with CBD resulted in a significant reduction in tonic, tonic-clonic and focal seizures without impairment in patients with ADNFLE with DEPDC5 mutation.

BRIEF SUMMARY OF THE DISCLOSURE

In accordance with a first aspect of the present invention there is provided a cannabidiol (CBD) preparation for use in the treatment of seizures associated with autosomal dominant nocturnal frontal lobe epilepsy (ADNFLE) with DEPDC5 mutation.

In a further embodiment, the seizures associated with ADNFLE with DEPDC5 mutation are tonic, tonic-clonic and focal seizures without impairment.

In a further embodiment, the CBD preparation comprises greater than 95% (w/w) CBD and not more than 0.15% (w/w) tetrahydrocannabinol (THC).

Preferably the CBD preparation comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

Preferably the CBD preparation is used in combination with one or more concomitant anti-epileptic drugs (AED).

Preferably the one or more AED is vigabatrin and/or carbamazepine.

In one embodiment the CBD is present is isolated from cannabis plant material. Preferably at least a portion of at least one of the cannabinoids present in the CBD preparation is isolated from cannabis plant material.

In a further embodiment the CBD is present as a synthetic preparation. Preferably at least a portion of at least one of the cannabinoids present in the CBD preparation is prepared synthetically.

Preferably the dose of CBD is greater than 5 mg/kg/day. More preferably the dose of CBD is 20 mg/kg/day. More preferably the dose of CBD is 25 mg/kg/day. More preferably the dose of CBD is 50 mg/kg/day.

In accordance with a second aspect of the present invention there is provided a method of treating seizures associated with autosomal dominant nocturnal frontal lobe epilepsy (ADNFLE) with DEPDC5 mutation comprising administering a cannabidiol (CBD) preparation to the subject in need thereof.

DEFINITIONS

Definitions of some of the terms used to describe the invention are detailed below:

Over 100 different cannabinoids have been identified, see for example, Handbook of Cannabis, Roger Pertwee, Chapter 1, pages 3 to 15. These cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Tonic seizures" can be generalised onset, affecting both sides of the brain, or they can be focal onset, starting in just one side of the brain. If a tonic seizure starts in both sides of the brain, all muscles tighten and the subject's body goes stiff. If standing, they may fall to the floor, their neck may extend, eyes open wide and roll upwards, whilst their arms may raise upwards and legs stretch or contract. If a tonic seizure starts in one side of the brain muscles tighten in just one area of the body. Tonic seizures usually last less than one minute.

"Tonic-clonic seizures" consist of two phases: the tonic phase and the clonic phase. In the tonic phase the body becomes entire rigid, and in the clonic phase there is uncontrolled jerking. Tonic-clonic seizures may or may not be preceded by an aura, and are often followed by headache, confusion, and sleep. They may last mere seconds or continue for several minutes. These seizures are also known as a grand mal seizure.

"Focal Seizures" are defined as seizures which originate within networks limited to only one hemisphere. What happens during the seizure depends on where in the brain the seizure happens and what that part of the brain normally does.

"Focal seizures without impairment" are seizures which originate within networks limited to only one hemisphere where the awareness or responsiveness of the subject is not impaired.

DETAILED DESCRIPTION

Preparation Of Highly Purified CBD Extract

The following describes the production of the highly-purified (>95% w/w) cannabidiol extract which has a known and constant composition.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD. Although the CBD is highly purified because it is produced from a cannabis plant rather than synthetically there is a small number of other cannabinoids which are co-produced and co-extracted with the CBD. Details of these cannabinoids and the quantities in which they are present in the medication are as described in Table A below.

TABLE A

| Composition of highly purified CBD extract | |
| --- | --- |
| Cannabinoid | Concentration |
| CBD | >95% w/w |
| CBDA | NMT 0.15% w/w |
| CBDV | NMT 1.0% w/w |
| $\Delta^9$ THC | NMT 0.15% w/w |
| CBD-C4 | NMT 0.5% w/w |

>greater than
NMT-not more than

Preparation Of Botanically Derived Purified CBD

The following describes the production of the botanically derived purified CBD which comprises greater than or equal to 98% w/w CBD and less than or equal to other cannabinoids was used in the open label, expanded-access program described in Example 1 below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (botanically derived purified CBD).

The plant starting material is referred to as Botanical Raw Material (BRM); the botanical extract is the intermediate; and the active pharmaceutical ingredient (API) is CBD, the drug substance.

All parts of the process are controlled by specifications. The botanical raw material specification is described in Table B and the CBD API is described in Table C.

TABLE B

| CBD botanical raw material specification | | |
| --- | --- | --- |
| Test | Method | Specification |
| Identification: | | |
| A | Visual | Complies |
| B | TLC | Corresponds to standard (for CBD & CBDA) |
| C | HPLC/UV | Positive for CBDA |
| Assay: | In-house | NLT 90% of assayed |
| CBDA + CBD | (HPLC/UV) | cannabinoids by peak area |
| Loss on Drying | Ph.Eur. | NMT 15% |
| Aflatoxin | UKAS method | NMT 4 ppb |
| Microbial: | Ph.Eur. | NMT$10^7$ cfu/g |
| TVC | | NMT$10^5$ cfu/g |
| | | NMT$10^2$ cfu/g |
| Fungi | | |
| *E.coli* | | |
| Foreign Matter: | Ph.Eur. | NMT 2% |
| Residual Herbicides and Pesticides | Ph.Eur. | Complies |

TABLE C

| Test | Test Method | Limits |
|---|---|---|
| | | Specification of an exemplary botanically derived purified CBD preparation |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| CBDA | HPLC-UV | NMT 0.15% w/w |
| CBDV | | 0.2-1.0% w/w |
| THC | | 0.01-0.1% w/w |
| CBD-C4 | | 0.3-0.5% w/w |
| Residual Solvents: | | |
| Alkane | GC | NMT 0.5% w/w |
| Ethanol | | NMT 0.5% w/w |
| Residual Water | Karl Fischer | NMT 1.0% w/w |

The purity of the botanically derived purified CBD preparation was greater than or equal to 98%. The botanically derived purified CBD includes THC and other cannabinoids, e.g., CBDA, CBDV, CBD-C1, and CBD-C4.

In some embodiments, the CBD preparation comprises not more than 0.15% THC based on total amount of cannabinoid in the preparation. In some embodiments, the CBD preparation comprises about 0.01% to about 0.1% THC based on total amount of cannabinoid in the preparation. In some embodiments, the CBD preparation comprises about 0.02% to about 0.05% THC based on total amount of cannabinoid in the preparation.

In some embodiments, the CBD preparation comprises about 0.2% to about 1.0% CBDV based on total amount of cannabinoid in the preparation. In some embodiments, the CBD preparation comprises about 0.2% to about 0.8% CBDV based on total amount of cannabinoid in the preparation.

In some embodiments, the CBD preparation comprises about 0.3% to about 0.5% CBD-C4 based on total amount of cannabinoid in the preparation. In some embodiments, the CBD preparation comprises about 0.3% to about 0.4% CBD-C4 based on total amount of cannabinoid in the preparation.

In some embodiments, the CBD preparation comprises about 0.1% to about 0.15% CBD-C1 based on total amount of cannabinoid in the preparation.

Distinct chemotypes of the *Cannabis sativa* L. plant have been produced to maximize the output of the specific chemical constituents, the cannabinoids. Certain chemovars produce predominantly CBD. Only the (−)-trans isomer of CBD is believed to occur naturally. During purification, the stereochemistry of CBD is not affected.

Production of CBD Botanical Drug Substance

An overview of the steps to produce a botanical extract, the intermediate, are as follows:
a) Growing
b) Direct drying
c) Decarboxylation
d) Extraction—using liquid $CO_2$
e) Winterization using ethanol f) Filtration
g) Evaporation High CBD chemovars were grown, harvested, dried, baled and stored in a dry room until required. The botanical raw material (BRM) was finely chopped using an Apex mill fitted with a 1 mm screen. The milled BRM was stored in a freezer prior to extraction.

Decarboxylation of CBDA to CBD was carried out using heat. BRM was decarboxylated at 115° C. for 60 minutes.

Extraction was performed using liquid $CO_2$ to produce botanical drug substance (BDS), which was then crystalized to produce the test material. The crude CBD BDS was winterized to refine the extract under standard conditions (2 volumes of ethanol at −20° C. for approximately 50 hours). The precipitated waxes were removed by filtration and the solvent was removed to yield the BDS.

Production of Botanically Derived Purified CBD Preparation

The manufacturing steps to produce the botanically derived purified CBD preparation from BDS were as follows:
a) Crystallization using $C_5$-$C_{12}$ straight chain or branched alkane
b) Filtration
c) Vacuum drying The BDS produced using the methodology above was dispersed in $C_5$-$C_{12}$ straight chain or branched alkane. The mixture was manually agitated to break up any lumps and the sealed container then placed in a freezer for approximately 48 hours. The crystals were isolated via vacuum filtration, washed with aliquots of cold $C_5$-$C_{12}$ straight chain or branched alkane, and dried under a vacuum of <10 mb at a temperature of 60° C. until dry. The botanically derived purified CBD preparation was stored in a freezer at −20° C. in a pharmaceutical grade stainless steel container, with FDA food grade approved silicone seal and clamps.

Physicochemical Properties of the Botanically Derived Purified CBD

The botanically derived purified CBD used in the clinical trial described in the invention comprises greater than or equal to 98% (w/w) CBD and less than or equal to 2% (w/w)

of other cannabinoids. The other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

The botanically derived purified CBD used additionally comprises a mixture of both trans-THC and cis-THC. It was found that the ratio of the trans-THC to cis-THC is altered and can be controlled by the processing and purification process, ranging from 3.3:1 (trans-THC:cis-THC) in its unrefined decarboxylated state to 0.8:1 (trans-THC:cis-THC) when highly purified.

Furthermore, the cis-THC found in botanically derived purified CBD is present as a mixture of both the (+)-cis-THC and the (−)-cis-THC isoforms.

Clearly a CBD preparation could be produced synthetically by producing a composition with duplicate components.

Example 1 below describes the use of a botanically derived purified CBD in an open label, expanded-access program to investigate the clinical efficacy and safety of purified pharmaceutical cannabidiol formulation (CBD) in the treatment of ADNFLE with DEPDC5 mutation.

EXAMPLE 1: CLINICAL EFFICACY AND SAFETY OF PURIFIED PHARMACEUTICAL CANNABIDIOL (CBD) IN THE TREATMENT OF PATIENTS DIAGNOSED WITH ADNFLE WITH DEPDC5MUTATION

Study Design

The subject was required to be on one or more AEDs at stable doses for a minimum of two weeks prior to baseline and to have stable vagus nerve stimulation (VNS) settings and ketogenic diet ratios for a minimum of four weeks prior to baseline.

The patient was administered botanically derived purified CBD in a 100 mg/mL sesame oil-based solution at an initial dose of 9.9 milligrams per kilogram per day (mg/kg/day) in two divided doses. Dose was then increased weekly by 5 mg/kg/day to a goal of 20 to 25 mg/kg/day.

A maximum dose of 50 mg/kg/day could be utilised it they were tolerating the medication but had not achieved seizure control; the patient had further weekly titration by 5 mg/kg/day.

There was one patient in this study, and they received CBD for 24 weeks. Modifications were made to concomitant AEDs as per clinical indication.

Seizure frequency, intensity, and duration were recorded by caregivers in a diary during a baseline period of at least 28 days. Changes in seizure frequency relative to baseline were calculated after at least 2 weeks and at defined time-points of treatment.

Statistical Methods:

Patients may be defined as responders if they had more than 50% reduction in seizure frequency compared to baseline. The percent change in seizure frequency was calculated as follows:

$$\% \text{ change seizure frequency} = \frac{((\text{weekly seziure frequency time interval}) - (\text{weekly seizure frequency Baseline}))}{(\text{weekly seizure frequency Baseline})} \times 100$$

The percent change of seizure frequency may be calculated for any time interval where seizure number has been recorded. For the purpose of this example the percent change of seizure frequency for the end of the treatment period was calculated as follows:

$$\% \text{ reduction seizure frequency} = \frac{((\text{weekly seizure frequency Baseline}) - (\text{weekly seizure frequency End}))}{(\text{weekly seizure frequency Baseline})} \times 100$$

RESULTS

Patient Description

The patient enrolled in the open label, expanded-access program was diagnosed with ADNFLE and had DEPDC5 gene mutation. The patient experienced several different seizure types including tonic, tonic-clonic and focal seizures without impairment and was taking several concomitant AEDs.

The patient was 16 years old and he was male as detailed in Table 1 below.

TABLE 1

Patient demographics, seizure type and concomitant medication

| Patient Number | Age (years) | Sex | Seizure types | Concomitant AEDs |
|---|---|---|---|---|
| 1 | 16.17 | M | Tonic, tonic-clonic, focal without impairment | CBM, VGB |

VGB = vigabatrin,
CBM = carbamazepine

Study Medication and Concomitant Medications

The patient on the study was titrated up to 25.8 mg/kg/day of CBD. The patient was on two concomitant AEDs at the time of starting CBD.

Clinical Changes

Table 2 illustrates the seizure frequency for the patient as well as the dose of CBD given.

TABLE 2

Seizure frequency data for Patient 1
Patient 1

| | | Seizure Type | | |
|---|---|---|---|---|
| Time | Tonic | Tonic-clonic | Focal without impairment | Dose CBD (mg/kg/day) |
| Baseline | 117.0 | 88.0 | 12.0 | — |
| 2 weeks | 54.0 | 84.0 | 2.0 | 9.9 |
| 4 weeks | 117.0 | 77.0 | 0.2 | 21.3 |
| 8 weeks | 84.0 | 63.0 | 32.8 | 25.5 |
| 12 weeks | 84.8 | 68.0 | 30.8 | 25.5 |
| 16 weeks | 96.8 | 74.8 | 2.0 | 25.8 |
| 24 weeks | 99.2 | 68.0 | 4.0 | 19.6 |

Patient 1 was treated for 24 weeks and experienced a 15.2% reduction in tonic seizures, a 22.7% reduction in tonic-clonic seizures and a 66.7% reduction in focal seizures without impairment over the treatment period.

Overall, the patient reported reductions of 15.2-66.7% in seizures over period of treatment with CBD. The average reduction in seizure frequency was 34.9%. CBD was effective in reducing the frequency of tonic, tonic-clonic and focal seizures without impairment.

CONCLUSIONS

These data indicate that CBD was able to significantly reduce the number of seizures associated with ADNFLE with DEPDC5 mutation. Clearly the treatment is of significant benefit in this difficult to treat epilepsy syndrome given the high response rate experienced in all patients.

In conclusion, this study signifies the use of CBD for treatment of seizures associated with ADNFLE with DEPDC5 mutation. Seizure types include tonic, tonic-clonic and focal seizures without impairment for which seizure frequency rates decreased by significant rates, by up to 67%.

The invention claimed is:

1. A method for treating seizures associated with autosomal dominant nocturnal frontal lobe epilepsy (ADNFLE) with DEPDC5 mutation, the method comprising administering a cannabidiol (CBD) drug substance to a patient in need thereof, wherein the CBD drug substance comprises greater than 95% (w/w) CBD, and wherein the CBD drug substance provides a dose of CBD in the range of 5 mg/kg/day to 50 mg/kg/day.

2. The method of claim 1, wherein the seizures associated with ADNFLE with DEPDC5 mutation are tonic, tonic-clonic and focal seizures without impairment.

3. The method of claim 1, wherein the CBD drug substance comprises not more than 0.15% (w/w) tetrahydrocannabinol (THC).

4. The method of claim 1, wherein the CBD drug substance comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

5. The method of claim 1, wherein the CBD drug substance is used in combination with one or more concomitant anti-epileptic drugs (AED).

6. The method of claim 5, wherein the one or more AED is vigabatrin and/or carbamazepine.

7. The method of claim 1, wherein the CBD is isolated from cannabis plant material.

8. The method of claim 1, wherein the CBD drug substance comprises at least one cannabinoid in addition to CBD, and at least a portion of at least one of the non-CBD cannabinoids present in the CBD drug substance is isolated from cannabis plant material.

9. The method of claim 1, wherein the CBD is present as a synthetic preparation.

10. The method of claim 9, wherein the CBD drug substance comprises at least one cannabinoid in addition to CBD, and at least a portion of at least one of the non-CBD cannabinoids present in the drug substance is prepared synthetically.

11. The method of claim 1, wherein the dose of CBD is in the range of 5 mg/kg/day to 25 mg/kg/day.

12. The method of claim 1, wherein the dose of CBD is 20 mg/kg/day.

13. The method of claim 1, wherein the dose of CBD is 25 mg/kg/day.

14. The method of claim 1, wherein the dose of CBD is 50 mg/kg/day.

15. The method of claim 1, wherein the dose of CBD is in the range of 10 mg/kg/day to 25 mg/kg/day.

* * * * *